(12) United States Patent
Grass et al.

(10) Patent No.: US 7,676,018 B2
(45) Date of Patent: Mar. 9, 2010

(54) EFFICIENT ITERATIVE FOUR-DIMENSIONAL CARDIAC CONE-BEAM CT RECONSTRUCTION

(75) Inventors: Michael Grass, Buchholz iin der Nordheide (DE); Andy Ziegler, Hamburg (DE); Tim Nielsen, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 243 days.

(21) Appl. No.: 12/065,615

(22) PCT Filed: Sep. 1, 2006

(86) PCT No.: PCT/IB2006/053055

§ 371 (c)(1),
(2), (4) Date: Mar. 4, 2008

(87) PCT Pub. No.: WO2007/031899

PCT Pub. Date: Mar. 22, 2007

(65) Prior Publication Data

US 2008/0267342 A1    Oct. 30, 2008

(30) Foreign Application Priority Data

Sep. 13, 2005    (EP)    ................... 05108408

(51) Int. Cl.
*A61B 6/00*    (2006.01)
(52) U.S. Cl. .............................. 378/8; 378/4
(58) Field of Classification Search ...... 378/4, 378/8, 15
See application file for complete search history.

(56) References Cited

U.S. PATENT DOCUMENTS

| | | |
|---|---|---|
| 2003/0007593 A1 | 1/2003 | Heuscher |
| 2003/0161436 A1* | 8/2003 | Boyd et al. ............... 378/8 |
| 2004/0081270 A1* | 4/2004 | Heuscher ............... 378/4 |
| 2005/0111622 A1 | 5/2005 | Bruder |
| 2006/0198491 A1* | 9/2006 | Taguchi ............... 378/15 |

FOREIGN PATENT DOCUMENTS

WO    2005008597 A2    1/2005

OTHER PUBLICATIONS

Bruder, H., et al.; A Novel Reconstruction Scheme for Cardiac Volume Imaging with MSCT Providing Cone Correction; 2002; SPIE: Medical Imaging-Image Processing; vol. 4684:60-73.

Nielsen, T., et al.; Iterative Cardiac Cone-Beam CT Reconstruction; 2004; SPIE Medical Imaging-Image Processing; vol. 5370:2003-2014.

* cited by examiner

*Primary Examiner*—Edward J Glick
*Assistant Examiner*—Alexander H Taningco

(57) ABSTRACT

The increasing cone angle of current high-end and future CT systems leads to a decrease in image quality if approximate cone-beam reconstruction methods are used. According to an exemplary embodiment of the present invention, an iterative four-dimensional cardiac CT reconstruction is provided, in which phase volumes are selected from the four-dimensional data set, each having the same spatial volume at different phase points. Corresponding voxels inside these phase volumes are then forward projected onto the same projection. After calculation of a different projection, these voxels are updated. This may provide for an efficient implementation of an iterative four-dimensional cardiac cone-beam CT reconstruction.

17 Claims, 4 Drawing Sheets

EFFICIENT ITERATIVE FOUR-DIMENSIONAL CARDIAC CONE-BEAM CT RECONSTRUCTION

The invention relates to the field of X-ray imaging. In particular, the invention relates to an examination apparatus for examination of an object of interest, to an image processing device, to a method of examining an object of interest, to a computer-readable medium and to program element.

The increasing cone angle of current high-end and future CT systems leads to a decrease in image quality if approximate cone-beam reconstruction methods are used. For the case of cardiac cone-beam CT, exact reconstruction is not feasible and therefore, iterative reconstruction methods are a potential candidate for this application. They deliver excellent image quality for large cone angles and they can increase the signal-to-noise ratio (SNR) of the reconstructed images.

However, application of such iterative reconstruction methods is limited by their high computational effort. In particular for the four-dimensional reconstruction of moving objects, where the complete volume has to be reconstructed for a number of phase points, this problem is severe.

It may therefore be desirable to have an efficient iterative image reconstruction of four-dimensional data sets.

According to an exemplary embodiment of the present invention, an examination apparatus for examination of an object of interest may be provided, the examination apparatus comprising an acquisition unit for acquiring a four-dimensional data set of the object of interest and a calculation unit adapted for selecting a first phase volume and a second phase volume from the four-dimensional data set, forward projecting a first voxel of the first phase volume on the basis of a first set of coefficients, forward projecting a second voxel of the second phase volume on the basis of a second set of coefficients, updating the forward projected first voxel on the basis of a third set of update coefficients and updating the forward projected second voxel on the basis of a fourth set of update coefficients, wherein the first voxel and the second voxel have the same spatial coordinates but different phase points.

Therefore, according to this exemplary embodiment of present invention, an examination apparatus may be provided which is adapted for performing an iterative reconstruction of a four-dimensional data set of an object of interest which reconstruction may be efficiently implemented in hardware. Since the first voxel and the second voxel both have the same spatial coordinates and only differ in their phase points (since they are selected from different phase volumes), the forward projecting of both voxels as well as the back-projection or updating of both voxels may efficiently be performed. Forward projecting and updating voxels having the same spatial coordinates (wherein the forward projecting of the voxels may be performed in a first step and wherein the updating of both voxels may be performed in a second step) may result in a decrease of computational effort.

According to another exemplary embodiment of the present invention, the calculation unit is further adapted for calculating a weighting function, resulting in a first weight corresponding to the first phase volume and in a second weight corresponding to the second phase volume.

Thus, according to this exemplary embodiment of the present invention, a first weight for the first phase volume and a second weight for the second phase volume may be calculated during one calculation step (and thus basically simultaneously).

According to another exemplary embodiment of the present invention, the calculation unit is further adapted for calculating the first set of coefficients for mapping the first voxel of the first phase volume onto a projection and for calculating the second set of coefficients for mapping the second voxel of the second phase volume onto the projection.

Therefore, the coefficients for the first voxel and the coefficients for the second voxel may be calculated at the same calculation step. Since both voxels have the same spatial coordinates, this calculation step may be very efficient.

According to another exemplary embodiment of the present invention, the calculation unit is further adapted for calculating a difference projection on the basis of a first projection and a second projection and for calculating the first set of update coefficients and the second set of update coefficients on the basis of the difference projection.

Therefore, according to this exemplary embodiment of the present invention, the difference projection may be calculated for a complete stack of phase dependent projections.

According to another exemplary embodiment of the present invention, the difference projection is multiplied by a corresponding cardiac weight.

According to another exemplary embodiment of the present invention, the examination apparatus further comprises an electrocardiogram unit adapted for acquiring electrocardiogram data, wherein the weighting function is a cardiac weighting function for the first phase and the second phase.

Thus, according to this exemplary embodiment of the present invention, the weighting function corresponds to the heartbeat of the object of interest (which, in this case, may be a patient). This may provide for an efficient reduction of motion artefacts.

According to another exemplary embodiment of the present invention, the weighting function is a function of at least one of a projection number from the electrocardiogram data, scan parameters, a field of view size, and a field of view position.

Thus, according to this exemplary embodiment of the present invention, the weighting function reflects at least the electrocardiogram data, the scan parameters of the data acquisition process, or size or position of the field of view.

According to another exemplary embodiment of the present invention, the first phase volume and the second phase volume have the same spatial volume but at different phase points.

For example, both phase volumes have the size (nx,ny,nz), where nx(ny,nz) describe the number of voxel in the x(y,z) dimension. But both phase volumes are acquired at different phase points (times).

According to another exemplary embodiment of the present invention, the first weight and the second weight are greater than zero.

Therefore, according to this exemplary embodiment of the present invention, only those phase volumes are selected from the multi-phase data set, which have, for this projection, a cardiac weight greater than zero and define a corresponding set of phase dependent projections.

According to another exemplary embodiment of the present invention, the examination apparatus further comprises an electromagnetic radiation source adapted for emitting electromagnetic radiation to the object of interest and a collimator arranged between the electromagnetic radiation source and the acquisition unit, wherein the collimator is adapted for collimating an electromagnetic radiation beam emitted by the electromagnetic radiation source to form a fan-beam or a cone-beam.

According to another exemplary embodiment of the present invention, the examination apparatus is adapted as a cardiac cone beam computed tomography apparatus.

Furthermore, according to another exemplary embodiment of the present invention, the four-dimensional data set comprises a first subset and a second subset, wherein the first and the second subset each has a size corresponding to a subset size for non-gated iterative reconstruction multiplied by a mean cardiac cycle length and divided by a mean gating window width.

This leads to a subset size, which may provide for a similar convergence speed as for the non-gated reconstruction. If the subset size of the non-gated reconstruction is optimal with respect to e.g. image quality, it is also appropriate for the gated reconstruction.

According to another exemplary embodiment of the present invention, the examination apparatus is configured as one of the group consisting of a baggage inspection apparatus, a medical application apparatus, a material testing apparatus and a material science analysis apparatus. A field of application of the invention may be material science analysis, since the defined functionality of the invention may allow for a fast, efficient and highly accurate analysis of a material.

According to another exemplary embodiment of the present invention, a method of examination of an object of interest is provided, the method comprising the steps of acquiring a four-dimensional data set of the object of interest, selecting a first phase volume and a second phase volume from the four-dimensional data set, forward projecting a first voxel of the first phase volume on the basis of a first set of coefficients, forward projecting a second voxel of the second phase volume on the basis of a second set of coefficients, updating the forward projected first voxel on the basis of a third set of update coefficients and updating the forward projected second voxel on the basis of a fourth set of update coefficients, wherein the first voxel and the second voxel have the same spatial coordinates but different phase points.

According to another exemplary embodiment of the present invention, an image processing device for examination of an object of interest may be provided, the image processing device comprising a memory for storing a four-dimensional data set of the object of interest. Furthermore, the image processing device may comprise a calculation unit, adapted for carrying out the above-mentioned method steps.

Therefore, an image processing device may be provided which is adapted for performing an efficient iterative reconstruction of an object of interest on the basis of a four-dimensional data set.

According to another exemplary embodiment of the present invention, a computer-readable medium may be provided, in which a computer program of examination of an object of interest is stored which, when being executed by a processor, is adapted to carry out the above-mentioned method steps.

Furthermore, the present invention relates to a program element of examination of an object of interest, which may be stored on a computer-readable medium. The program element may be adapted to carry out the above-mentioned method steps.

The program element may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that phase volumes are selected from the multi-phase data set, wherein each phase volume has the same spatial volume but at different phase points. In each of these phase volumes one voxel is identified having the same spatial coordinates but different phase points. This set of voxels is then forward projected from all different cardiac phase volumes onto the projections, which are defined as an array of the phase. After calculating a difference projection, a back-projection is performed (again parallel for the whole set of voxels with the same spatial coordinates).

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

Figure 1:
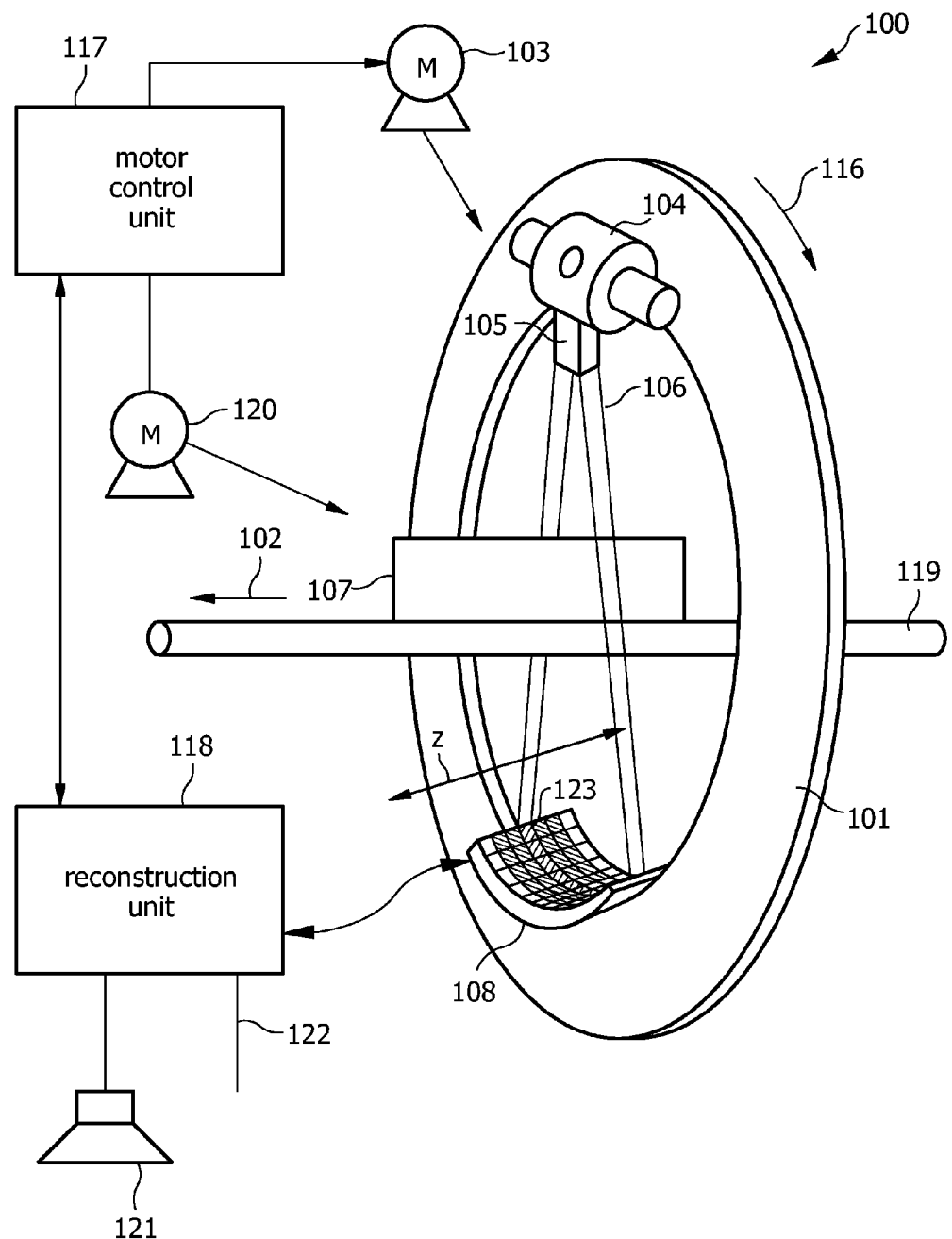
FIG. 1 shows a simplified schematic representation of a CT scanner system according to an exemplary embodiment of the present invention.

FIG. 1 shows an exemplary embodiment of a CT scanner system according to an exemplary embodiment of the present invention. With reference to this exemplary embodiment, the present invention will be described for the application in medical imaging. However, it should be noted that the present invention is not limited to this application, but may also be applied in the field of baggage inspection, or other industrial applications, such as material testing.

The computer tomography apparatus 100 depicted in FIG. 1 is a cone-beam CT scanner. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits a polychromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the centre of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the cone-beam 106. The detector 108, which is depicted in FIG. 1, comprises a plurality of detector elements 123 each capable of detecting, in an energy-resolving manner, X-rays or individual photons which have penetrated the object of interest 107.

During a scan of the object of interest 107, the source of radiation 104, the aperture system 105 and the detector 108 are rotated along the gantry 101 in the direction indicated by arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 may be a patient or an item of baggage which is disposed on a conveyor belt 119. During the scan of the object of interest 107, while the gantry 101 rotates around the item of baggage 107, the conveyor belt 119 displaces the object of interest 107 along a direction parallel to the rotational axis 102 of the gantry 101. By this, the object of interest 107 is scanned along a helical scan path. The conveyor belt 119 may also be stopped during the scans to thereby measure single slices. Instead of providing a conveyor belt 119, for example, in medical applications where the object of interest 107 is a patient, a movable table may be used. However, it should be noted that in all of the described cases it may also be possible to perform other scan paths such as the saddle trajectory by moving the table periodically back and forth at twice the frequency of the source-detector arrangement.

The detector 108 may be connected to the calculation unit 118. The calculation unit 118 may receive the detection result, i.e. the read-outs from the detector elements 123 of the detector 108 and may determine a scanning result on the basis of the read-outs. Furthermore, the calculation unit 118 communicates with the motor control unit 117 in order to coordinate the movement of the gantry 101 with motors 103 and 120 with the conveyor belt 119.

The calculation unit 118 may be adapted for iteratively reconstructing an image of the object of interest, according to an exemplary embodiment of the present invention. A reconstructed image generated by the reconstruction unit 118 may be output to a display (not shown in FIG. 1) via an interface 122.

The calculation unit 118 may be realized by a data processor to process read-outs from the detector elements 123 of the detector 108.

Furthermore, as may be taken from FIG. 1, the reconstruction unit 118 may be connected to a loudspeaker 121, for example, to automatically output an alarm in case of the detection of suspicious material in the item of baggage 107.

The computer tomography apparatus 100 for examination of the object of interest 107 includes the detector 108 having the plurality of detecting elements 123 arranged in a matrix-like manner, each being adapted to detect X-rays. Furthermore, the computer tomography apparatus 100 comprises the determination unit or reconstruction unit 118 adapted for reconstructing an image of the object of interest 107.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. The detecting elements 123 form a multi-slice detector array 108.

Figure 2:
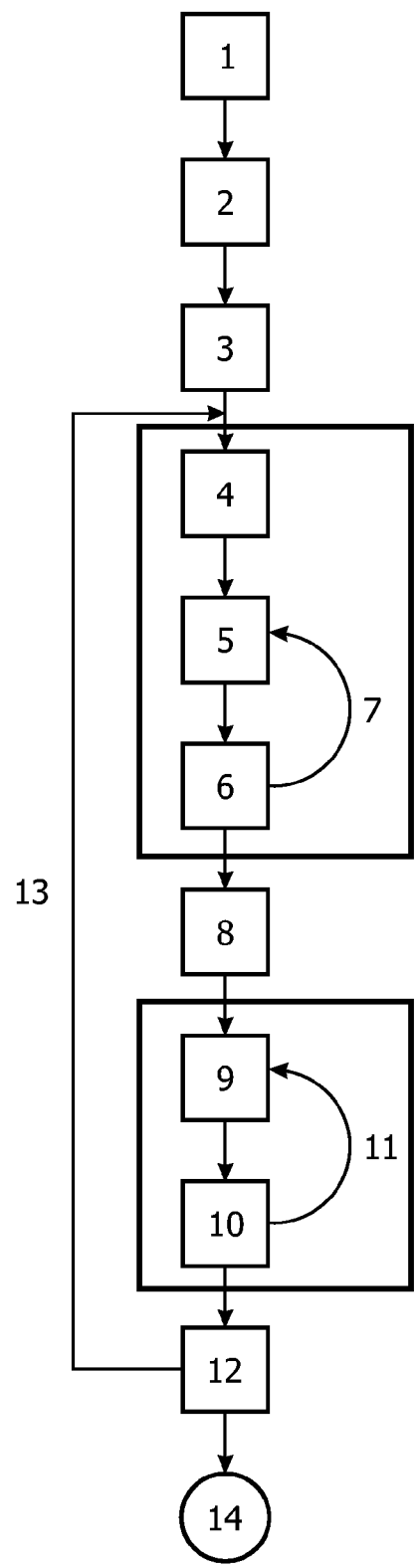
FIG. 2 shows a flow-chart representing a method according to an exemplary embodiment of the present invention.

FIG. 2 shows a method according to an exemplary embodiment of the present invention. Due to the limited temporal resolution, in the case of cardiac cone-beam reconstruction the number of cardiac phases which are reconstructed to generate a four-dimensional data set is greater than the length of the cardiac cycle divided by the mean gating window width. Consequently, the non-zero weighting values of the cardiac gating functions for different cardiac phases are overlapping.

A further reason for overlapping cardiac gating functions may be that the cardiac phases are selected such that their distance corresponds to a time resolution of the measurement and that the gating function for the whole cardiac cycle is non-zero.

According to an exemplary embodiment of the present invention, the method starts with step 1, with the definition of the cardiac volume of interest $f(x,y,z)$ to be reconstructed as multi-phase volume $f(x,y,z,t)$ with the size $(nx,ny,nz,nt)$. Here, nx(ny,nz) describes the number of the voxel in the x(y,z) dimension and nt describes the number of phases.

Then, in step 2, the subset size for ordered subset iterative reconstruction is defined as the subset size used for a non-gated iterative reconstruction multiplied by the ratio of the mean cardiac cycle length and the mean gating window width.

Then, in step 3, the cardiac weighting function is calculated for each of the cardiac phases as a function of the projection number from the ECG values, the scan parameters and the field of view size and position.

After that, in step 4, those volumes from the multi-phase data set are selected, which have—for this projection—a cardiac weight greater than zero and define a corresponding set of phase dependent projections.

Figure 3:
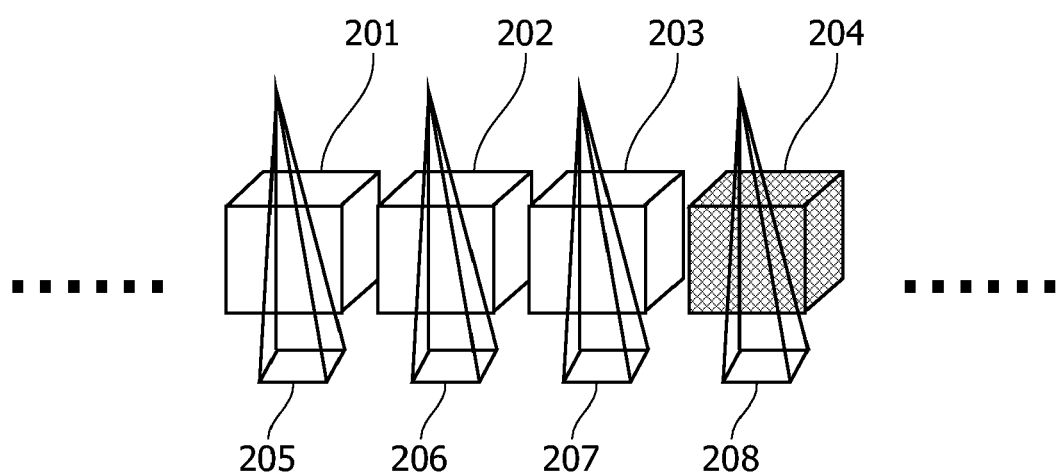
FIG. 3 shows a schematic representation of a projection geometry for a single voxel and a selected projection.

Such a set of volumes 201, 202, 203, 204 is depicted in FIG. 3, which shows a schematic representation of a projection geometry for a single voxel and a selected projection. Each of the volumes 201 to 204 has the same spatial volume at different phase points. Furthermore, as schematically depicted by projections 205, 206, 207, 208, each phase volume 201 to 204 is related to the same projection 205 to 208.

Then, in step 5, the coefficients for mapping a voxel value at a position $(x,y,z)$ in these phase volumes 201, 202, 203, 204 onto the projection are calculated.

After that, in step 6, these calculated coefficients are applied to forward project the voxel from all different cardiac phase volumes 201 to 204 onto the projections, which are defined as an array of the phase.

Steps 5 and 6 are repeated until all voxels of the phase volumes 201 to 204 are projected onto this particular projection for all phases under consideration.

Furthermore, the cycle comprising steps 4 to 7 is repeated for each projection in the subset.

Then, in step 8, the difference projection for the complete stack of phase dependent projections is calculated and multiplied by the cardiac weight for all projections of this subset.

For each projection in the subset the following steps 9 to 11 are performed.

In step 9, the coefficients required for the update of a single voxel in the volume are calculated from this projection.

In step 10, the coefficients are used for updating the voxel in all volumes which have a non-zero cardiac weight for this projection.

Then, in step 11, steps 9 and 10 are repeated for each voxel until the complete volume is updated. The method then jumps to step 12.

The method steps 4 to 12 are repeated for all of the subsets in step 13.

After that, the method jumps to step 14, where it ends.

Figure 4:
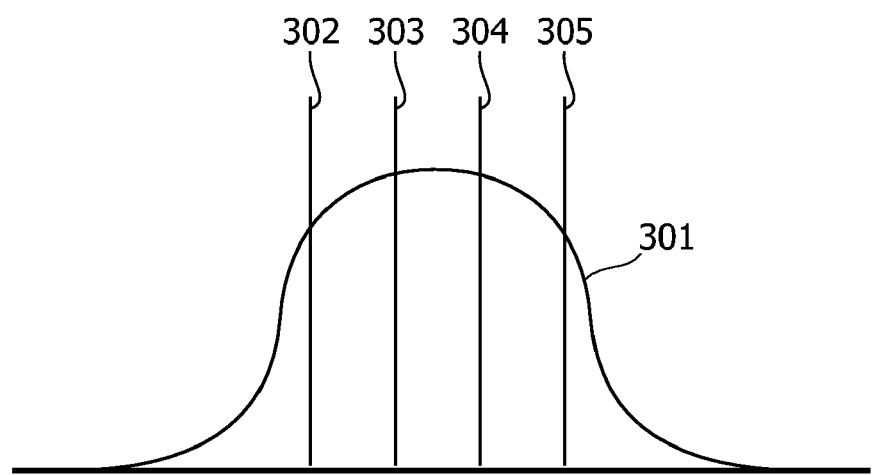
FIG. 4 shows a schematic representation of a cardiac weight function.

FIG. 4 shows a schematic representation of a cardiac weighting function 301. Vertical lines 302, 303, 304, 305 represent different phase points corresponding to the four phase volumes depicted in FIG. 3. As may be seen from the cardiac weighting function 301, each phase volume corresponds to a different cardiac weight.

Figure 5:
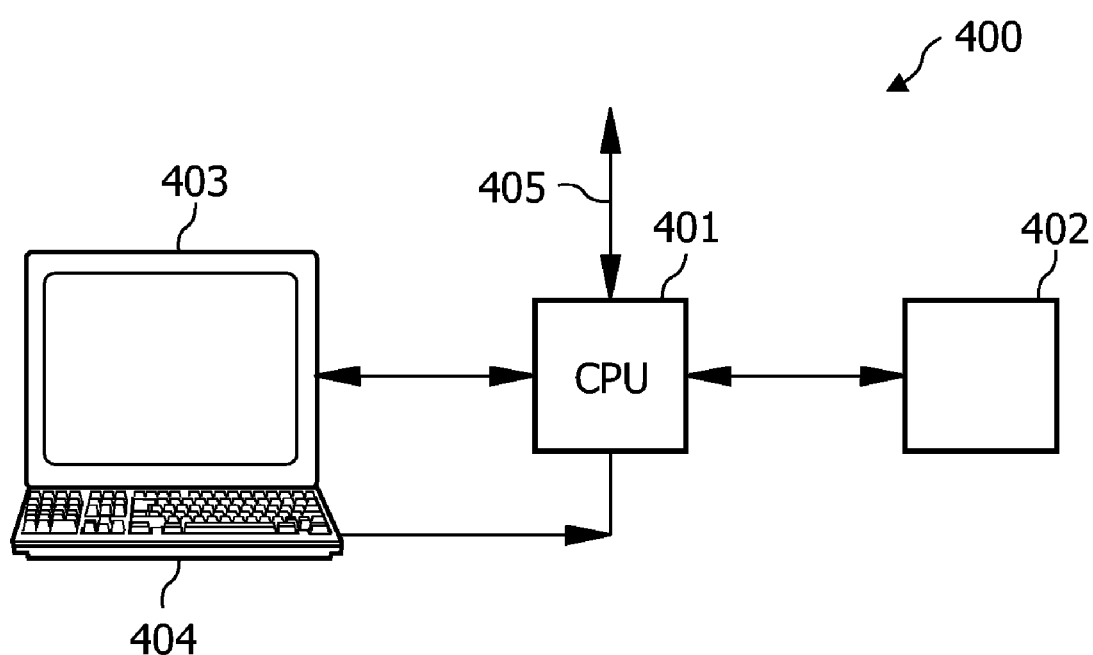
FIG. 5 shows an exemplary embodiment of an image processing device according to the present invention, for executing an exemplary embodiment of a method in accordance with the present invention.

FIG. 5 show an exemplary embodiment of an image processing device according to the present invention for executing an exemplary embodiment of the method in accordance with the present invention. The image processing device 400 depicted in FIG. 5 comprises a central processing unit (CPU) or image processor 401 connected to a memory 402 for storing an image depicting an object of interest, such as a breast or other piece of tissue. The data processor 401 may be connected to a plurality of input/output network for diagnosis devices, such as an CT device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 5.

Furthermore, via the bus system 405, it may also be possible to connect the image processing and control processor 401 to, for example, a motion monitor, which monitors a motion of the object of interest. For example, the motion sensor may be an exhalation sensor or an electrocardiogram unit.

Exemplary embodiments of the invention may be sold as a software option to imaging work stations.

The examination apparatus, the image processing device, the method, the program element and the computer-readable medium according to exemplary embodiments of the present invention may provide for an improved image quality and higher speed in iterative cardiac cone-beam CT reconstruction. For example, 50 cardiac phases to be reconstructed and a mean gating window width of 20% cardiac cycle may result again in reconstruction speed of a factor of 10.

It should be noted that the term "comprising" does not exclude other elements or steps and the "a" or "an" does not exclude a plurality and that a single processor or system may fulfill the functions of several means or units recited in the claims. Also elements described in association with different embodiments may be combined.

It should also be noted, that any reference signs in the claims shall not be construed as limiting the scope of claims.

The invention claimed is:

1. An examination apparatus for examination of an object of interest, the examination apparatus comprising:
    an acquisition unit for acquiring a four-dimensional data set of the object of interest;
    a calculation unit adapted for:
    selecting a first phase volume and a second phase volume from the four-dimensional data set;
    forward projecting a first voxel of the first phase volume on the basis of a first set of coefficients;
    forward projecting a second voxel of the second phase volume on the basis of a second set of coefficients;
    updating the forward projected first voxel on the basis of a third set of update coefficients;
    updating the forward projected second voxel on the basis of a fourth set of update coefficients;
    wherein the first voxel and the second voxel have the same spatial coordinates but different phase points.

2. The examination apparatus of claim 1,
    wherein the calculation unit is further adapted for:
    calculating a weighting function, resulting in a first weight corresponding to the first phase volume and in a second weight corresponding to the second phase volume.

3. The examination apparatus of claim 1,
    wherein the calculation unit is further adapted for:
    calculating the first set of coefficients for mapping the first voxel of the first phase volume onto a projection;
    calculating the second set of coefficients for mapping the second voxel of the second phase volume onto the projection.

4. The examination apparatus of claim 1,
    wherein the calculation unit is further adapted for:
    calculating a difference projection on the basis of a first projection and a second projection; and
    calculating the first set of update coefficients and the second set of update coefficients on the basis of the difference projection.

5. The examination apparatus of claim 4,
    wherein the difference projection is multiplied by a corresponding cardiac weight.

6. The examination apparatus of claim 2, further comprising:
    an electrocardiogram unit adapted for acquiring electrocardiogram data;
    wherein the weighting function is a cardiac weighting function for the first phase and the second phase.

7. The examination apparatus of claim 6,
    wherein the weighting function is a function of at least one of a projection number from the electrocardiogram data, scan parameters, a field of view size, and a field of view position.

8. The examination apparatus of claim 1,
    wherein the first phase volume and the second phase volume have the same spatial volume but at different phase points.

9. The examination apparatus of claim 1,
    wherein the first weight and the second weight are greater than zero.

10. The examination apparatus claim 1, further comprising:
    an electromagnetic radiation source adapted for emitting electromagnetic radiation to the object of interest; and
    a collimator arranged between the electromagnetic radiation source and the acquisition unit;
    wherein the collimator is adapted for collimating an electromagnetic radiation beam emitted by the electromagnetic radiation source to form a fan-beam or a cone-beam.

11. The examination apparatus of claim 1,
    wherein the examination apparatus is adapted as a cardiac cone beam computed tomography apparatus.

12. The examination apparatus of claim 1,
    wherein the four-dimensional data set comprises a first subset and a second subset;
    wherein the first and the second subset each has a size corresponding to a subset size for non-gated iterative reconstruction multiplied by a mean cardiac cycle length and divided by a mean gating window width.

13. The examination apparatus of claim 1, configured as one of the group consisting of a baggage inspection apparatus, a medical application apparatus, a material testing apparatus and a material science analysis apparatus.

14. An image processing device for examination of an object of interest, the image processing device comprising:
    a memory for storing a four-dimensional data set of the object of interest;
    a calculation unit adapted for:
    selecting a first phase volume and a second phase volume from the four-dimensional data set;
    forward projecting a first voxel of the first phase volume on the basis of a first set of coefficients;
    forward projecting a second voxel of the second phase volume on the basis of a second set of coefficients;
    updating the forward projected first voxel on the basis of a third set of update coefficients;
    updating the forward projected second voxel on the basis of a fourth set of update coefficients;

wherein the first voxel and the second voxel have the same spatial coordinates but different phase points.

15. A method of examination of an object of interest, method comprising the steps of:
acquiring a four-dimensional data set of the object of interest;
selecting a first phase volume and a second phase volume from the four-dimensional data set;
forward projecting a first voxel of the first phase volume on the basis of a first set of coefficients;
forward projecting a second voxel of the second phase volume on the basis of a second set of coefficients;
updating the forward projected first voxel on the basis of a third set of update coefficients;
updating the forward projected second voxel on the basis of a fourth set of update coefficients;
wherein the first voxel and the second voxel have the same spatial coordinates but different phase points.

16. A computer-readable medium, in which a computer program of examination of an object of interest is stored which, when being executed by a processor, is adapted to carry out the steps of:
acquiring a four-dimensional data set of the object of interest;
selecting a first phase volume and a second phase volume from the four-dimensional data set;
forward projecting a first voxel of the first phase volume on the basis of a first set of coefficients;
forward projecting a second voxel of the second phase volume on the basis of a second set of coefficients;
updating the forward projected first voxel on the basis of a third set of update coefficients;
updating the forward projected second voxel on the basis of a fourth set of update coefficients;
wherein the first voxel and the second voxel have the same spatial coordinates but different phase points.

17. A program element of examination of an object of interest, which, when being executed by a processor, is adapted to carry out the steps of:
acquiring a four-dimensional data set of the object of interest;
selecting a first phase volume and a second phase volume from the four-dimensional data set;
forward projecting a first voxel of the first phase volume on the basis of a first set of coefficients;
forward projecting a second voxel of the second phase volume on the basis of a second set of coefficients;
updating the forward projected first voxel on the basis of a third set of update coefficients;
updating the forward projected second voxel on the basis of a fourth set of update coefficients;
wherein the first voxel and the second voxel have the same spatial coordinates but different phase points.

* * * * *